United States Patent
Johnson et al.

[11] Patent Number: 5,928,196
[45] Date of Patent: Jul. 27, 1999

[54] CONTROL MODULE CASSETTE LOCKS AND METHODS

[75] Inventors: Jay Gregory Johnson, Maple Plain; Orbert S. Smith, Princeton, both of Minn.

[73] Assignee: SIMS Deltec, Inc., St. Paul, Minn.

[21] Appl. No.: 08/698,236

[22] Filed: Aug. 14, 1996

[51] Int. Cl.⁶ .................................................. A61M 1/00
[52] U.S. Cl. ........................ 604/153; 417/477.2; 604/151
[58] Field of Search ..................... 604/131, 151, 604/153, 132; 128/DIG. 12; 417/234, 477.2, 477.3; 220/337

[56] References Cited

U.S. PATENT DOCUMENTS

| | | | |
|---|---|---|---|
| 3,402,673 | 9/1968 | Ballentine et al. | |
| 3,559,644 | 2/1971 | Stoft et al. | |
| 3,620,650 | 11/1971 | Shaw | 417/417 |
| 4,187,057 | 2/1980 | Xanthopoulos | 417/63 |
| 4,236,880 | 12/1980 | Archibald | 417/478 |
| 4,482,347 | 11/1984 | Borsanyi | 604/153 |
| 4,559,038 | 12/1985 | Berg et al. | 604/153 |
| 4,565,542 | 1/1986 | Berg | 604/131 |
| 4,585,399 | 4/1986 | Baier | 417/477 |
| 4,650,469 | 3/1987 | Berg et al. | 604/131 |
| 4,657,486 | 4/1987 | Stempfle et al. | 604/153 |
| 4,671,792 | 6/1987 | Borsanyi | 604/153 |
| 5,017,059 | 5/1991 | Davis | 409/131 |
| 5,074,756 | 12/1991 | Davis | 604/153 |
| 5,078,683 | 1/1992 | Sancoff et al. | 604/67 |
| 5,165,874 | 11/1992 | Sancoff et al. | 604/153 |
| 5,213,483 | 5/1993 | Flaherty et al. | 604/153 |
| 5,226,886 | 7/1993 | Skakoon et al. | 604/153 |
| 5,330,431 | 7/1994 | Herskowitz | 604/153 |
| 5,336,190 | 8/1994 | Moss et al. | 604/153 |
| 5,397,222 | 3/1995 | Moss et al. | 604/153 X |
| 5,425,173 | 6/1995 | Moss et al. | 604/151 |
| 5,482,446 | 1/1996 | Williamson et al. | 604/153 |
| 5,509,901 | 4/1996 | Milijasevic | 604/153 |
| 5,531,697 | 7/1996 | Olsen et al. | 604/131 |
| 5,540,561 | 7/1996 | Johnson | 604/153 |
| 5,564,915 | 10/1996 | Johnson | 417/572 |
| 5,567,119 | 10/1996 | Johnson | 604/153 |

FOREIGN PATENT DOCUMENTS

| | | |
|---|---|---|
| WO 93/10853 | 6/1993 | WIPO . |
| WO 96/27402 | 9/1996 | WIPO . |
| WO 97/02059 | 1/1997 | WIPO . |

OTHER PUBLICATIONS

Photographs of a pump product by Patient Solutions, Inc., Med–Mate™, Model 1100, pp. A1–A–5.

Photographs of a pump product by Block Medical, Inc., a Hillenbrand Industry, Verifuse® Model No. B001500, pp. B1–B3.

Photographs of a pump product by Medfusion, Inc., a Medex, Inc. Company, Infu–Med™, WalkMed™ 440 PIC, pp. C1–C2.

(List continued on next page.)

*Primary Examiner*—Ronald Stright, Jr.
*Assistant Examiner*—A. T. Nguyen
*Attorney, Agent, or Firm*—Merchant, Gould, Smith, Edell, Welter & Schmidt, P.A.

[57] ABSTRACT

A medical infusion pump system includes a clamshell housing, a plate, and a pump. The clamshell housing includes a first shell and a second shell hingedly connected together allowing the housing to be in an open position or in a closed position. The housing defines one open end and an interior space. A plate releasably engages the housing at the open end when the housing is in the closed position. The plate defines an opening communicating with the interior space and includes attachment structure. The pump is removably attachable to the attachment structure of the plate and includes a retaining portion. When the pump is attached to the plate, the retaining portion retains the housing in the closed position.

14 Claims, 4 Drawing Sheets

OTHER PUBLICATIONS

Photographs of a pump product by C.R. Bard Inc., Medsystems Division, pp. D1–D3.

Photographs of a pump product by Pharmacia Deltec, Inc., pp. E1–E2.

Photographs of a pump product by AVI, Inc., AVI Guardian™ MICRO 110, pp. F1–F4.

Photographs of a pump product by Abbott Laboratories, Abbott/Shaw LifeCare®Pump Model 3, pp. G1–G3.

Patient Solutions, Inc. literature for MedMate™ 1100, 2 pp.

Patient Solutions, Inc. Directions for Use, MedMate™ model 1100, 61 pp.

Block Medical, Inc. literature for Verifuse System, 1 p., dated Nov. 1990.

Medfusion, Inc. Operations Manual for Medfusion Walkmed™ Ambulatory Infusion Pump, 92 pp., dated Apr., 1990.

Medex Ambulatory Infusion Systems literature, entitled "WalkMed Pump Disposable Products," 2 pp., dated 1992.

Medex Ambulatory Infusion Systems literature, entitled "WalkMed PCA," 2 pp., dated 1993.

Bard Ambulatory PCA Pump literature, 2 pp. dated Jun. 1990.

Bard MedSystems Division, C.R. Bard, Inc., Quick Reference Guide, 2 pp., dated Feb. 1992.

Bard MedSystems Division, C.R. Bard, Inc., Bard® Ambulatory PCA Pump Operator's Manual, 43 pp., dated Apr. 1990.

AVI, Inc. literature entitled "The AVI Advantage,", 2 pp., dated 1983.

AVI, Inc. literature, entitled "Bridging the Gap," 6 pp., dated Apr. 22, 1983.

Abbott Laboratories Hospital Products Division literature, entitled "The Blue Line System LifeCare®, "16 pp., dated Jul., 1990.

Abbott Laboratories Hospital Products Division literature, entitled "LifeCare® Electronic Flow Control Systems Catalog," 34 pp., dated May, 1985.

CONTROL MODULE CASSETTE LOCKS AND METHODS

FIELD OF THE INVENTION

This invention relates generally to medical devices. More particularly, this invention relates to a reusable cassette and security system for a pump and methods of use.

BACKGROUND OF THE INVENTION

In medical applications, it is sometimes necessary to deliver fluid intravenously to a patient undergoing treatment. The fluid may be contained in a bag or other fluid reservoir, conveyed through a tube, and inserted into the patient's vein. At times, the amount of fluid conveyed to the patient must be controlled or regulated. In those instances where the fluid to the patient must be controlled, control modules, or pumps, have been used.

One control module, or pump, is described in U.S. Pat. No. 4,559,038. This pump controls the delivery of fluid from the reservoir to the patient. In the '038 patent, the fluid is in a bag held in a cassette immediately adjacent to the pump. The pump controls the amount of fluid to the patient by physically pressuring the tube from the bag to the patient, and restricting the volume of fluid allowed to flow to the patient. The pump includes a pump mechanism which engages the tube and squeezes the tube against a pressure plate of the cassette to effect pumping of fluid.

In the past, certain types of cassettes and pressure plates have been used to connect the pump to the tube. It is often desirable that access to the tube be limited to the medical professionals treating the patient. Because of this reason, and other reasons such as safety and cleanliness, the cassette is permanently attached to the pressure plate and the tube, with the reservoir contained securely in the cassette. When the fluid reservoir is empty, or the treatment to the patient completed, the cassette, reservoir, tube, and pressure plate are all thrown away. Disposing of the cassette contributes to waste and expense. There is a need for reusable cassettes that allow for replacement of a used reservoir and tube. There is also a need to limit access to the reservoir, such as in the case of hazardous drugs or controlled substances.

SUMMARY OF THE INVENTION

The invention comprises a medical infusion pump system including a clamshell housing, a pressure plate, and a pump. The clamshell housing includes a first shell and a second shell hingedly connected together allowing the housing to be in an open position or in a closed position. The housing defines one open end and an interior space. The pressure plate releasably engages the housing at the open end when the housing is in the closed position. The pressure plate defines an opening communicating with the interior space and includes attachment structure. The pump is removably attachable to the attachment structure of the pressure plate and includes a retaining portion. When the pump is attached to the pressure plate, the retaining portion retains the housing in the closed position. The attachment structure on the pressure plate may include a pair of hooks and a loop on opposite ends of the pressure plate.

Preferably, the retaining portion of the pump includes a skirt. When the pump is attached to the plate, the skirt overlaps the housing to retain the housing in the closed position. The pressure plate and housing preferably include a tab and slot arrangement such that each tab is engaged by the skirt to retain the housing in the closed position.

Preferably, the interior space holds a reservoir having a tube. The pressure plate may further include a channel for holding the tube, wherein the tube passes from the reservoir in the interior space of the housing, through the opening, and into the channel.

Preferably, the housing includes at least one post and the pressure plate includes at least one hole; and the pressure plate releasably engages the housing by mating the hole with the post. The post and hole arrangement prevents the pressure plate from being separated from the housing in the closed position.

In another aspect, the invention comprises a method for using a medical infusion pump system. The method includes the steps of providing a clamshell housing having a first shell hingedly attached to a second shell, the housing defining an interior space and an open end; pivoting the first shell away from the second shell to expose the interior space; placing a reservoir in the interior space, the reservoir including an outlet tube; attaching a pressure plate to the first and second shells at the open end to close the housing; and attaching a pump to the pressure plate, the pump including a skirt for retaining the housing in a closed position.

Preferably, the step of attaching a pressure plate to the first and second shells includes attaching one edge of the pressure plate to the second shell; pivoting the first shell toward the pressure plate; and attaching a second edge of the pressure plate to the first shell.

Preferably, the method also includes the step of placing the reservoir outlet tube through an opening in the pressure plate.

In another aspect, the invention comprises a cassette including a first shell, a second shell, and a hinge. The first shell has a first main surface and two opposing first side surfaces attached to the first main surface. The second shell has a second main surface and two opposing second side surfaces attached to the second main surface. The hinge connects the first shell to the second shell so that the first side surfaces abut the second side surfaces, and the first shell and second shell define an interior space and an open end, wherein the open end is opposing the hinge.

Preferably, the open end is configured for receipt of a pressure plate. The first and second shells may include a pair of posts configured for mating with cooperating holes in the pressure plate to retain the pressure plate with the first and second shells in the closed position. The first and second shells may each include a tab at the open end to be engaged by the pump.

DETAILED DESCRIPTION OF THE PREFERRED EMBODIMENTS

Figure 2:
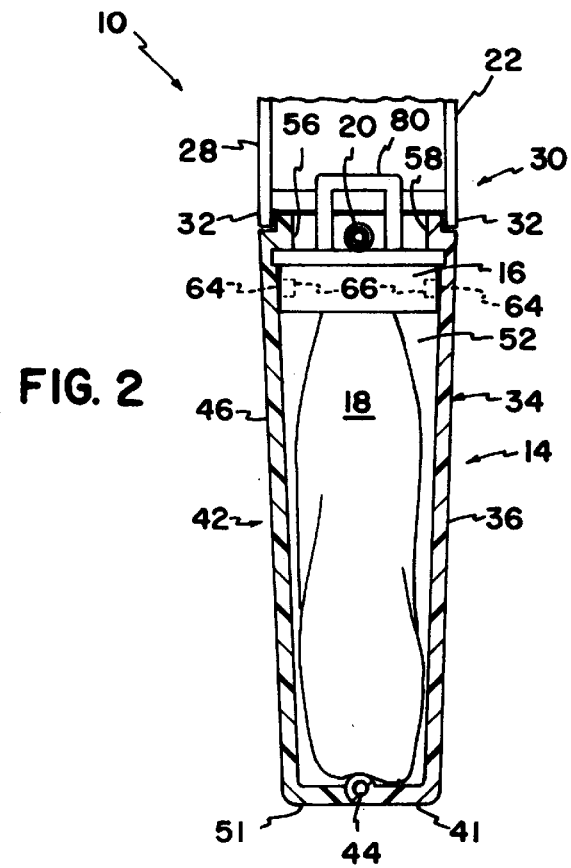
FIG. 2 is a partial cross-sectional view of FIG. 1 according to the present invention.

The invention relates to a medical infusion pump system including a cassette, a pressure plate, and a pump. The cassette, pressure plate, and pump may be part of a system for conveying fluid from a fluid reservoir, to a tube, and finally to the patient, such as the patient's vein. The cassette is reusable with the pump to pump fluid through different tubes, which tubes can be disposed of after use. The cassette is designed to be openable and closable in order to allow the user to remove used fluid reservoirs to be replaced by new fluid reservoirs. The cassette includes a mounting arrangement with the pump such that unauthorized access to the contents of the cassette is prevented.

Reference will now be made in detail to the present preferred embodiment of the invention wherein like reference numerals indicate like elements through the several views. As embodied herein, a medical infusion pump system is shown generally at 10. System 10 includes a control module, or pump 12, a hinged cassette 14 movable between an open and a closed position (FIG. 3), and a pressure plate 16. Pump 12 controls the amount of fluid conveyed from a fluid reservoir 18 through a tube 20 (FIG. 4) to the patient.

Figure 6:
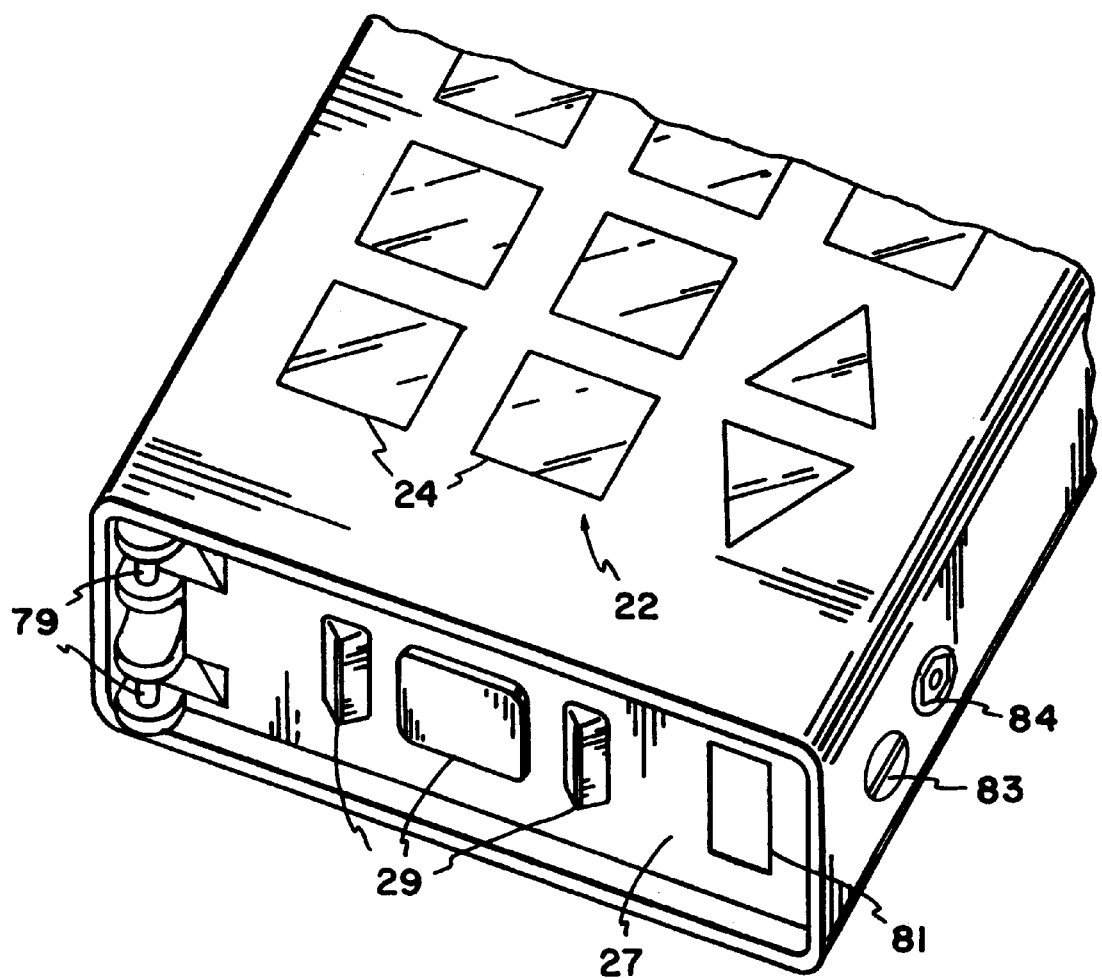
FIG. 6 is a further perspective view of the pump.

Pump 12 includes a control and display face 22. Control and display face 22 includes various control keys or buttons 24 for operating pump 12, and includes a display 26 for providing input and output information to the pump operator. Orthogonal to control and display face 22 is a tube interface region 27, as best shown in FIG. 6. Tube interface region 27 includes tube engaging members 29 for applying pressure to tube 20 in order to control the volume of fluid conveyed from fluid reservoir 18 to the patient. On the opposite side of control face 22 is a back face 28.

Figure 1:
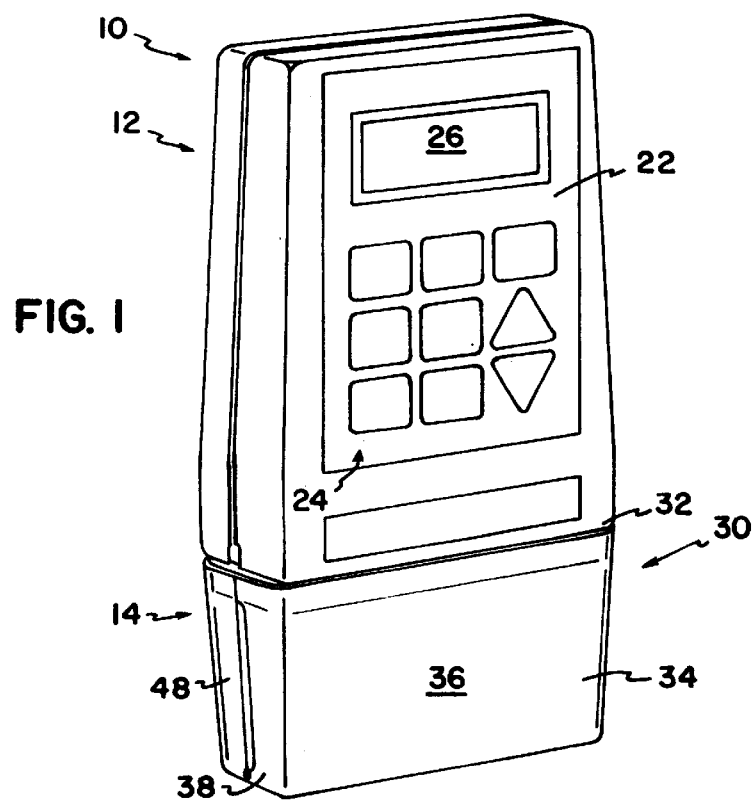
FIG. 1 is a perspective view of an embodiment of a system according to the present invention.

In accordance with the invention, the pump includes a retaining portion for retaining the cassette in a closed position. The retaining portion may include a variety of mechanical structures, so long as it accomplishes the function of keeping the cassette in a closed position. In one preferred arrangement shown in FIGS. 1 and 2, a retaining portion is shown generally at 30. In this particular preferred arrangement, retaining portion 30 includes a skirt 32. Skirt 32 is a pair of opposed lips and is a rigid section integral with the pump housing which projects beyond the end of control and display face 22 and back face 28. As will be explained in more detail below, when cassette 14 is attached to pump 12, skirt 32 overlaps cassette 14 and retains cassette 14 in a closed position. This prevents unauthorized access to the contents of the cassette, and yet still provides for a reusable cassette.

In accordance with the invention, the cassette includes a clamshell housing with a first shell and a second shell hingedly attached to each other. As embodied herein, cassette 14 may be a clamshell design having a first shell 34 and second shell 42. First shell 34 includes a first main surface 36, and a pair of first side surfaces 38, 40 substantially orthogonal to first main surface 36. Second shell 42 is connected to first shell 34 with a hinge 44. Second shell 42 includes a second main surface 46 bordered by a pair of second side surfaces 48, 50 substantially orthogonal thereto. Bottom surfaces 41, 51 form a bottom portion of each respective shell 34, 42 and meet at hinge 44.

Figure 3:
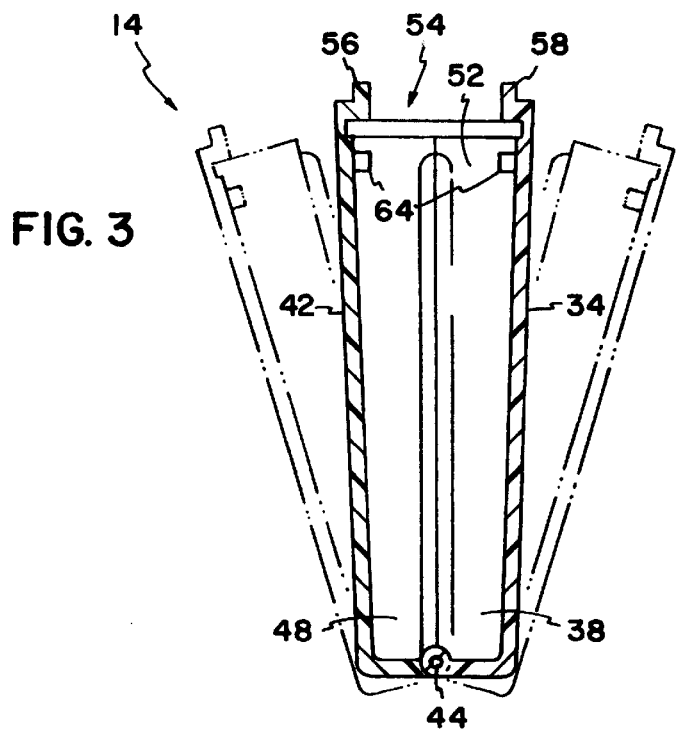
FIG. 3 is a cross-sectional view of one embodiment of a cassette according to the present invention.
Figure 4:
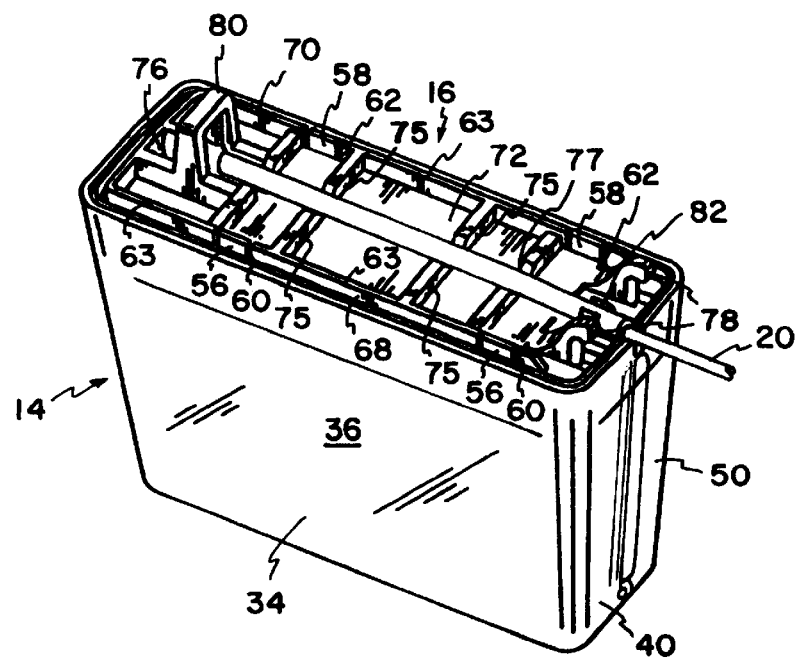
FIG. 4 is a perspective view the cassette of FIG. 3 attached to a pressure plate and enclosing a reservoir according to the present invention.

First shell 34 and second shell 42 cooperate to define an interior space 52, which is for holding fluid reservoir 18. First shell 34 and second shell 42 mate together in a way such that first side surface 38 abuts second side surface 48 (FIGS. 1 and 3), and first side surface 40 abuts second side surface 50 (FIG. 4). Preferably, the side surfaces overlap, to prevent needle access sites. First shell 34 and second shell 42, when mated together, define one open end 54 (FIG. 5) configured for receiving pressure plate 16. Open end 54 is on a side of cassette 14 which is opposing hinge 44. Hinge 44 allows cassette 14 to be in an open position, shown in phantom in FIG. 3, or a closed position shown in FIGS. 1–4. In the open position, access is allowed to interior space 52 to allow for the replacement of fluid reservoir 18. In the closed position, when attached to pump 12, skirt 32 prevents first shell 34 and second shell 42 from being pivoted about hinge 44, thereby trapping cassette 14 in the closed position. In the preferred embodiment, hinge 44 extends the length of cassette 14. Snaps or other locking features may be provided to hold shells 34, 42 together in the closed position before mounting cassette 14 to pump 12.

Figure 5:
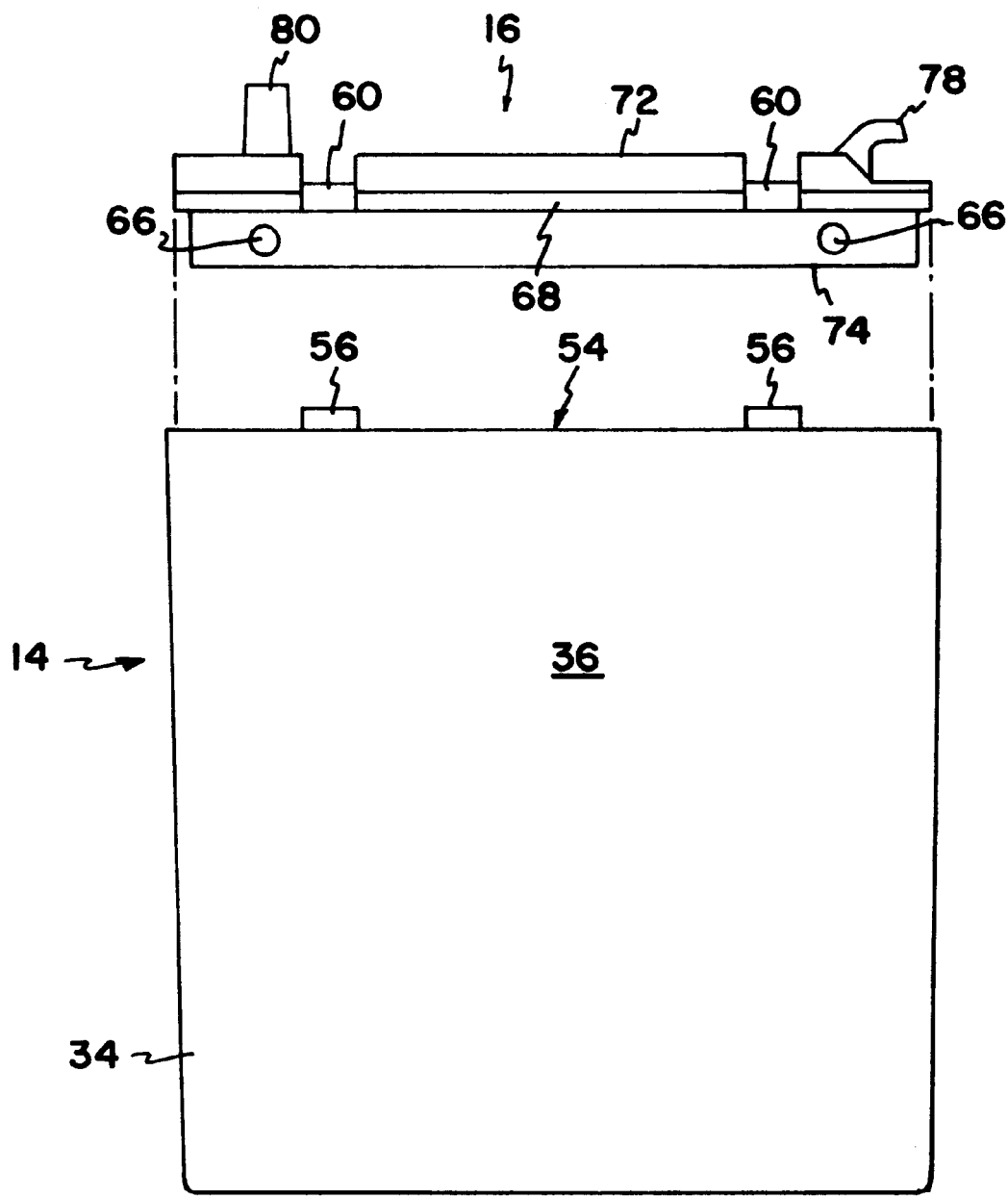
FIG. 5 is an elevational exploded view of the cassette and pressure plate of FIG. 4 according to the present invention.

First shell 34 includes at least one tab and preferably a pair of first tabs 56 extending beyond the end of first main surface 36 in the region of open end 54. Second shell 42 includes at least one tab and preferably a pair of second tabs 58 extending beyond the end of second main surface 46. First and second tabs 56, 58 engage mating slots 60, 62 which are defined by pressure plate 16. Tabs 56, 58 are the portion of first and second shells 34, 42 trapped by skirt 32 to keep cassette 14 in the closed position. In this manner, pressure plate 16 can include an integral strengthening rib 63 in the areas around the periphery of pressure plate 16 except for slots 60, 62. To keep shells 34, 42 and pressure plate 16 from being separated, at least one post and preferably a plurality of posts 64, shown in FIG. 3, are provided. Posts 64 engage mating holes 66 in pressure plate 16 (FIG. 5). Posts 64 and holes 66 keep pressure plate 16 from being pulled out of open end 54 when shells 34, 42 are in the closed position. Other constructions are possible to prevent pull-out, such as lips extending from shells 34, 42 and overhanging a surface of pressure plate 16. Also, the posts and holes can be reversed in their locations. When pressure plate 16 is fitted in open end 54 and all of the tab and slots, and the holes and posts are engaged, it has a tight connection, as illustrated in FIG. 4. At least one tab per shell and at least one post per shell is preferable if the pressure plate is releasably joined to each shell. The functions of these structures can be combined, if desired.

Pressure plate 16 is substantially rectangular and includes first and second elongated edges 68, 70, a top surface 72, and a bottom surface 74. Pressure plate defines an opening 76 communicating with interior space 52, which allows tube 20 to pass through from fluid reservoir 18. Pressure plate 16 defines a channel 77 in top surface 72 and is formed by rib pairs 75. Channel 77 functions to hold tube 20 in a secure position so that the tube engaging mechanisms on pump 12 may function to control volume. Attachment structure for attaching pressure plate 16 to pump 12 includes a pair of hooks 78 and a loop 80. Hooks 78 engage pins 79 at one end of tube interface region 27 of pump 12, and loop 80 is selectively engaged by a latch internal to pump 12 at cavity 81 at an opposite end.

Pressure plate 16 of the inventive system may be either a disposable type of pressure plate, or one designed to be reusable. If reusable, pressure plate 16 can be permanently mounted to either first or second shells 34, 42. If pressure plate 16 is reusable, it is desirable although not required to either provide loop 80 with a slot or provide top and bottom surfaces 72, 74 with a slot extending to one of the side edges 68, 70 downstream from loop 80 so as to communicate with opening 76. This allows a used tube and reservoir to be separated from pressure plate 16 without having to thread the tube through opening 76 and loop 80. For reusable pressure plates, a clip 82 for releasably holding the tube is desired at the downstream end of pressure plate 16. If pressure plate 16 is not desired to be reusable, tube 20 can be permanently attached to pressure plate 16, such as by adhesive, or a solvent bond. After use, the tube and pressure plate 16 would be discarded, and shells 34, 42 reused with a new tube and pressure plate.

If the pressure plate is reusable, suitable materials for its construction are desired so as to ensure proper mounting to the pump and proper fluid delivery. The material or materials selected should withstand repeated reuses with the pump a suitable number of times and also allow the pump to pump properly without free flow or without requiring excessive energy drain and/or causing a stoppage of the pumping mechanism. All metal, molded plastic with metal reinforcement, and glass-filled plastic are possible constructions for a reusable pressure plate.

In operation, the medical infusion pump system is used as follows: Cassette 14 is provided with its first and second hinged shells 34, 42. One of the shells is pivoted away from the other shell to expose interior space 52. Reservoir 18 is placed in interior space 52. Unless previously attached to one of the shells, pressure plate 16 is attached to the first and second shells 34, 42 at open end 54 to close the housing by attaching one elongated edge 68 to second shell 42, pivoting first shell 34 toward pressure plate 16, and attaching the other elongated edge 70 to first shell 34. If pressure plate 16 was previously permanently attached to second shell 42, then first shell 34 is pivoted toward second shell to mount elongated edge 70 to first shell 34. In either situation, before pressure plate 16 is completely attached to both of first and second shells 34, 42, tube 20 may be placed in opening 76 in pressure plate 16 if not previously placed there. Next, pump 12 is attached to pressure plate 16 with hooks 78 and loop 80. Pump 12 is locked into position on the pressure plate through a latch engaging loop 80 and operated by latch button 83. Skirt 32 overlaps first and second shells 34, 42. The latch which engages loop 80 can be placed in the locked state by the medical professional using lock 84, so as to prevent unauthorized unlatching. Because pump 12 is locked to pressure plate 16, an unauthorized person is precluded from pivoting open cassette 14 and gaining access to the interior. As soon as access to cassette 14 is desired, cassette 14 is removed from pump 12, thereby allowing the shells to be pivoted apart. A new tube and reservoir, or a new pressure plate with tube and reservoir can be inserted and used with shells 34, 42 and pump 12.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical infusion pump system comprising:
   a cassette having a clamshell housing and a pressure plate,
   the clamshell housing including a first shell and a second shell, the first shell being hingedly connected to the second shell allowing the housing to be in an open position or in a closed position, the housing defining one open end and an interior space;
   the pressure plate engaging the housing at the open end when the housing is in the closed position, the pressure plate defining an opening communicating with the interior space, and the pressure plate including attachment structure; and
   a pump removably attachable to the attachment structure of the pressure plate to mount the cassette to the pump, the pump including a retaining portion, wherein when the pump is attached to the pressure plate, the retaining portion retains the housing in the closed position, wherein the retaining portion of the pump includes a skirt, wherein when the pump is attached to the pressure plate, the skirt overlaps the housing to retain the housing in the closed position.

2. The system of claim 1, wherein the first and second shells include a plurality of upwardly extending spaced apart tabs which are retained by the retaining portion of the pump, the pressure plate defining a plurality of slots, the slots each receiving one tab.

3. The system of claim 1, wherein:
   the interior space of the housing holds a reservoir having a tube; and
   the pressure plate further includes a channel for holding the tube, wherein the tube passes from the reservoir in the interior space of the housing, through said opening, and into the channel.

4. The system of claim 1, wherein:
   the first shell has a first main surface bordered by first side surfaces substantially orthogonal to the first main surface; and
   the second shell has a second main surface bordered by second side surfaces substantially orthogonal to the second main surface.

5. The system of claim 1, wherein the pressure plate is substantially rectangular including first and second elongated edges, a top surface, and a bottom surface.

6. The system of claim 5, wherein the attachment structure includes a pair of hooks and a loop on the top surface.

7. The system of claim 1, wherein the housing includes a plurality of posts, the pressure plate includes a plurality of holes, and the pressure plate releasably engages the housing by mating the holes with the posts.

8. The system of claim 7, wherein the first and second shells include a plurality of upwardly extending spaced apart tabs which are retained by the retaining portion of the pump, the pressure plate defining a plurality of slots, the slots each receiving one tab.

9. A method for using a medical infusion pump system, the method comprising the steps of
   providing a cassette having a clamshell housing and a pressure plate, the housing having a first shell hingedly attached to a second shell, the housing defining an interior space and an open end;
   pivoting the first shell away from the second shell to expose the interior space;
   placing a reservoir in the interior space, the reservoir including an outlet tube;
   attaching the pressure plate to the first and second shells at the open end to close the housing; and
   attaching a pump to the cassette, wherein the pump is mounted to the pressure plate, the pump including a skirt for retaining the housing in a closed position, wherein the skirt overlaps the housing to retain the housing in the closed position.

10. The method of claim 9, further comprising the step of placing the reservoir outlet tube through an opening in the pressure plate.

11. The method of claim 9, wherein the step of attaching a pressure plate to the first and second shells includes:
   attaching one edge of the pressure plate to the second shell;
   pivoting the first shell toward the pressure plate; and
   attaching a second edge of the pressure plate to the first shell.

12. A method for using a medical infusion pump system, the method comprising the steps of:

providing a cassette including a housing with first and second portions moveable relative to one another for controlling access to an interior of the housing, the housing having an open position and a closed position;

mounting a pump having a pair of opposed retaining portions to the cassette; and trapping the housing of the cassette in the closed position between the opposed retaining portions of the pump wherein the first and second portions of the housing are not moveable relative to one another, wherein the opposed retaining portions of the pump include a skirt, wherein the skirt overlaps the housing to retain the housing in the closed position.

13. The method of claim 12, further comprising the step of inserting a reservoir inside of the cassette.

14. The method of claim 12, further comprising the step of attaching a pressure plate to the cassette.

* * * * *